(12) United States Patent
Bourrie et al.

(10) Patent No.: US 7,504,406 B2
(45) Date of Patent: Mar. 17, 2009

(54) DERIVATIVES OF PYRIDO[2,3-D]PYRIMIDINE, THE PREPARATION THEREOF, AND THE THERAPEUTIC APPLICATION OF THE SAME

(75) Inventors: Bernard Bourrie, Saint-Gely-du-Fesc (FR); Pierre Casellas, Montpellier (FR); Samir Jegham, Montferrier-sur-Lez (FR); Claude Muneaux, Les Matelles (FR); Pierre Perreaut, Saint-Clement-de-Riviere (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/955,583

(22) Filed: Dec. 13, 2007

(65) Prior Publication Data

US 2008/0176874 A1  Jul. 24, 2008

Related U.S. Application Data

(63) Continuation of application No. PCT/FR2006/001518, filed on Jun. 29, 2006.

(30) Foreign Application Priority Data

Jul. 1, 2005  (FR) .................................. 05 07032

(51) Int. Cl.
*C07D 471/04* (2006.01)
*A61K 31/519* (2006.01)
(52) U.S. Cl. ................................. 514/264.11; 544/279
(58) Field of Classification Search ............ 514/364.11; 544/279
See application file for complete search history.

(56) References Cited

U.S. PATENT DOCUMENTS

| | | | |
|---|---|---|---|
| 3,534,039 A | 10/1970 | Davoll | |
| 5,620,981 A | 4/1997 | Blankley et al. | |
| 5,733,913 A | 3/1998 | Blankley et al. | |
| 5,733,914 A | 3/1998 | Blankley et al. | |
| 5,952,342 A | 9/1999 | Blankley et al. | |
| 2007/0167469 A1 | 7/2007 | Bourrie et al. | |

FOREIGN PATENT DOCUMENTS

| | | |
|---|---|---|
| EP | 0 790 997 B1 | 3/2000 |
| WO | WO 96/15128 | 5/1996 |
| WO | WO 96/34867 | 11/1996 |
| WO | WO 01/55147 | 8/2001 |
| WO | WO 01/70741 A1 | 9/2001 |
| WO | WO 02/12238 A2 | 2/2002 |
| WO | WO 03/000011 | 1/2003 |
| WO | WO 2004/063195 A1 | 7/2004 |
| WO | WO 2004/085436 | 10/2004 |
| WO | WO 2005/105097 A2 | 11/2005 |
| WO | WO 2006/016067 A2 | 2/2006 |
| WO | WO 2007/080324 A3 | 7/2007 |

OTHER PUBLICATIONS

Schroeder et al, Soluble 2-Substituted Aminopyrido[2,3-d]pyrimidin-7-yl Ureas. Structure—Activity Relationships against Selected Tyrosine Kinases and Exploration of in Vitro and in Vivo Anticancer Activity, J. Med. Chem. 2001, (44), 1915-1926.
Thompson et al, Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases, J. Med. Chem. 2005, (48), 4628-4653.
U.S. Appl. No. 12/166,431, filed Jul. 2, 2008, Perreaut et al.
Alam, Fighting Cancer: 'Magic Bullets' on Target to Lead Market, Pharmalicensing.com (Mar. 8, 2005).
Anzali et al, 1. Endothelin antagonists: Search for Surrogates of Methylendioxyphenyl by Means of a Kohonen Neural Network, Bioorganic & Medicinal Chemistry Letters 8 (1998) pp. 11-16.
Lewell et al, Drug Rings Database with Web Interface. A Tool for Identifying Alternative Chemical Rings in Lead Discovery Programs, J. Med. Che. 2003, 46, pp. 3257-3274.
Mederski et al, 2. Endothelin Antagonists: Evaluation of 2,1,3-Benzothiadiazole as a Methylendioxyphenyl Bioisoster, Bioorganic & Medicinal Chemistry Letters 8 (1998) pp. 17-22.
Palmer et al, Structure-activity Relationships for 2-anilino-6-phenylpyrido[2,3-d]pyrimidin-7(8H)-ones as Inhibitors of the Cellular Checkpoint Kinase Wee1, Bioorganic & Medicinal Chemistry Letters 15 (2005) pp. 1931-1935.
Sicinski, Killer Breast Cancer Therapy Hope, BBC News/Health Jan. 21, 2006.
Walsh, No 'Magic Bullet' Cure for Cancer, BBC News, International Version, Medical Notes, Feb. 1, 2007.

*Primary Examiner*—Mark L Berch
*Assistant Examiner*—Cecilia M Jaisle
(74) *Attorney, Agent, or Firm*—Kelly L. Bender

(57) ABSTRACT

The invention relates to derivatives of pyrido[2,3-d]pyrimidine, to the preparation thereof, and to the therapeutic application of the same.

6 Claims, No Drawings

DERIVATIVES OF PYRIDO[2,3-D]PYRIMIDINE, THE PREPARATION THEREOF, AND THE THERAPEUTIC APPLICATION OF THE SAME

The present invention relates to pyrido[2,3-d]pyrimidine derivatives, to the preparation thereof and to the therapeutic use thereof.

Compounds derived from pyrido[2,3-d]pyrimidine are described in patent applications WO 01/55 147 and WO 03/000 011 and in patents EP-B-790 997 and U.S. Pat. No. 5,733,913. These compounds are potentially useful for treating cell proliferation conditions.

Thus, and according to a first aspect, a subject of the present invention is compounds corresponding to formula (I):

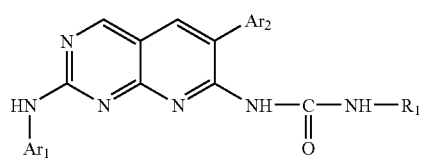

in which:
- $R_1$ is selected from a group comprising $(C_1-C_6)$alkyl, $(C_1-C_6)$alkyl$(C_3-C_7)$cycloalkyl, $CH_2COR_3$, phenyl, or phenyl substituted with hydroxyl and/or halogen and/or $(C_1-C_6)$alkyl;
- $R_3$ is a hydroxyl, $(C_1-C_4)$alkoxy, amino, $(C_1-C_4)$alkylamino or di$(C_1-C_4)$alkylamino group;
- $Ar_1$ is a radical selected from:

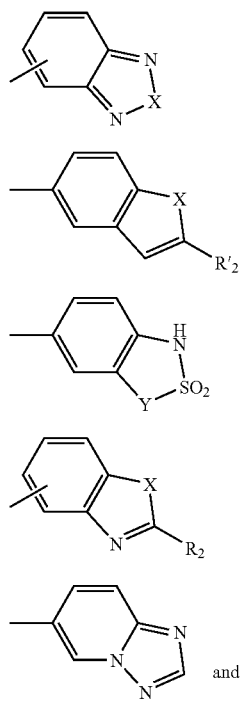

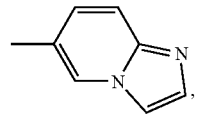

in which X is O or S, Y is $CH_2$ or NH, and $R_2$ is selected from the group comprising H, $(C_1-C_6)$alkyl or $(CH_2)_nNR_4R_5$, and $R'_2$ is $(CH_2)_nNR_4R_5$;

$R_4$ and $R_5$ are each, independently of one another, a substituent selected from H, $(C_1-C_4)$alkyl, $(C_1-C_6)$alkyl$(C_3-C_7)$cycloalkyl, $(C_3-C_7)$cycloalkyl, $C(=NH)NH_2$ and $SO_2(C_1-C_6)$alkyl, $R_5$ can also be a CO—$(C_1-C_4)$alkyl, CO—$(C_3-C_7)$cycloalkyl, CO-aryl, $SO_2$-aryl, tert-butoxycarbonyl or benzyloxycarbonyl group;

or $R_4$ and $R_5$, together with the nitrogen atom to which they are attached, constitute an azetidinyl, pyrrolidinyl, piperidinyl, piperazinyl or morpholinyl radical, said radical being unsubstituted or substituted one or more times with a $(C_1-C_6)$alkyl, $(C_1-C_4)$alkyl-OH or COO$(C_1-C_6)$ alkyl group;

$Ar_2$ is a phenyl group which is unsubstituted or substituted from 1 to 5 times with similar or different substituents selected from a halogen atom, a $(C_1-C_4)$alkyl group, a trifluoromethyl group or a $(C_1-C_4)$alkoxy group;

n is 1, 2 or 3.

According to a preferred variant, the compounds of formula (I) have a substituent $Ar_1$ which is a radical selected from:

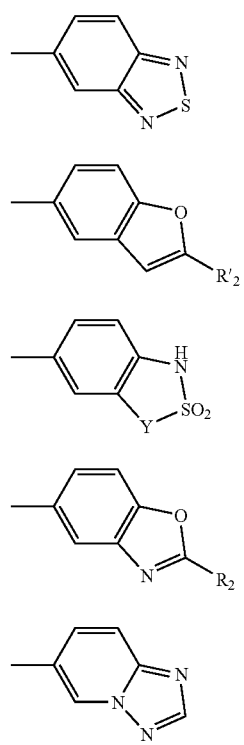

-continued f)

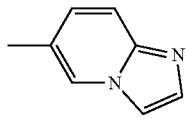

in which $R_2$ is $CH_3$ or $(CH_2)_nNR_4R_5$, and $R'_2$ is $CH_2NR_4R_5$, in which $R_4$ and $R_5$ are independently selected from H and $(C_1-C_6)$alkyl and Y is $CH_2$ or NH.

The products according to the invention advantageously have a substituent $Ar_2$ which is a radical:

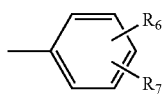

in which each $R_6$, $R_7$ is independently selected from the group comprising H, $CH_3$, $OCH_3$, F, Cl, Br. $R_6$ and $R_7$ are advantageously in the 2- and 6-position.

The products according to the invention advantageously have a substituent $Ar_2$ selected from phenyl, 2-methoxyphenyl, 2,6-dichlorophenyl, 3,5-dimethoxyphenyl, 3,4-dimethoxyphenyl, 2,6-dibromophenyl, 2-bromo-6-chlorophenyl, 2,4-dichlorophenyl, 3,5-dichlorophenyl, 2,6-dimethylphenyl and 2,6-difluorophenyl.

According to a preferred variant, the compounds of formula (I) have a substituent $Ar_1$ which is a radical selected from

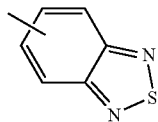

A compound that is more particularly preferred according to the invention is:

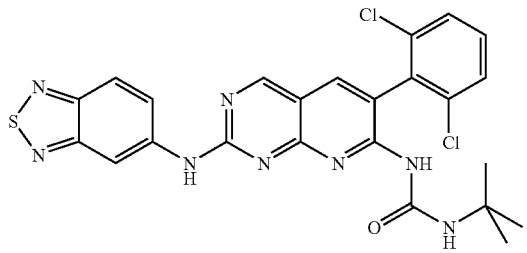

(N-[2-(2,1,3-benzothiadiazol-5-ylamino)-6-(2,6-dichlorophenyl)pyrido[2,3-d]pyrimidin-7-yl]-N'-(1,1-dimethylethyl)urea)

The compounds of the examples which follow are a subject of the present invention.

A compound in accordance with the invention can (i) be in a non-chiral form, or a racemic form, or a form enriched in one stereoisomer, or enriched in one enantiomer; (ii) be optionally salified, and (iii) be optionally hydrated or solvated.

The compounds of formula (I) can contain one or more asymmetrical carbon atoms.

They can therefore exist in the form of enantiomers or of diastereoisomers. These enantiomers and diastereoisomers and also mixtures thereof, including racemic mixtures, are part of the invention.

The compounds of formula (I) can exist in the form of bases or of addition salts with acids. When compounds of formula (I) contain free acid functions, for example carboxylic, sulphonic or phosphonic, these acid functions can be salified using bases so as to form addition salts. Such addition salts are part of the invention.

The addition salts with acids or with bases are advantageously prepared with, respectively, pharmaceutically acceptable acids or bases, but the salts of other acids or of bases that are useful, for example, for the purification or the isolation of the compounds of formula (I) are also part of the invention.

The compounds of formula (I) can also exist in the form of hydrates or of solvates, i.e. in the form of associations or of combinations with one or more molecules of water or with a solvent. Such hydrates and solvates are also part of the invention.

In the context of the present invention:

the term "a halogen atom" is intended to mean: a fluorine, a chlorine, a bromine or an iodine;

the term "an alkyl group" is intended to mean: a linear or branched, saturated aliphatic group. By way of example, mention may be made of methyl, ethyl, n-propyl, n-butyl, n-pentyl, n-hexyl, n-heptyl, 1-methylethyl, 1-methylpropyl, 2-methylpropyl, 1,1-dimethylethyl, 1-methylbutyl, 2-methylbutyl, 3-methylbutyl, 1,1-dimethylpropyl, 1,2-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, 1-ethyl-2-methylpropyl, 1-ethylbutyl, 2-ethylbutyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1-(1-methylethyl)butyl and 1-(1-methylethyl)-2-methylpropyl groups;

the term "a cycloalkyl group" is intended to mean: cyclopropyl, cyclobutyl, cyclopentyl, cyclohexyl, cycloheptyl, bicyclo[2.2.1]heptyl, cyclooctyl, bicyclo[2.2.2]octyl, bicyclo[3.2.1]octyl, adamantyl.

The compounds of formula (I) are prepared by reaction between a compound of formula (II):

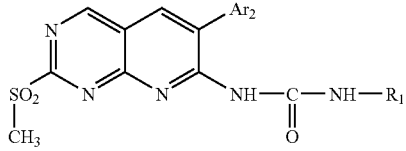

in which $R_1$ and $Ar_2$ are as defined for (I), and an amine of formula $Ar'_1NH_2$ (III) in which $Ar'_1$ is $Ar_1$, as defined for (I) or a precursor of $Ar_1$; where appropriate, the $Ar'_1$ group of the compound thus obtained is converted to an $Ar_1$ group.

In accordance with the invention, the compounds of formula (I) can be prepared according to a process characterized in that the following are reacted:
(i) a compound of formula:

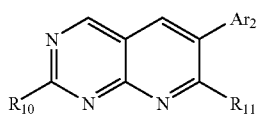

in which $R_{10}$ is a leaving group such as: (a) halogen, in particular Cl or Br, or (b) alkyl-S(O)m- with m=0, 1, or 2; $R_{11}$ is NHC(O)—NH—$R_1$; and
(ii) an amine of formula $Ar'_1NH_2$ (III) in which $Ar'_1$ is $Ar_1$ as defined for (I) or a precursor of $Ar_1$; where appropriate, the $Ar'_1$ group of the compound thus obtained is converted to an $Ar_1$ group.

When $R_{10}$ is halogen or alkyl-S(O)m-, with m=2, the reaction is carried out in a solvent, preferably a polar solvent:
(i) for example tetrahydrofuran, dimethyl sulphoxide or ethanol, optionally in the presence of a trace of acid such as hydrochloric acid; or
(ii) in dimethyl sulphoxide in the presence of a strong base such as tBuOK; at a temperature between ambient temperature and the reflux temperature of the solvent.

When $R_{10}$ is alkyl-S(O)m- with m=0 or 1, the reaction can be carried out with $Ar'_1NH_2$ (III) in the molten state, preferably at a temperature in the region of 200° C., without catalyst.

Where appropriate, the amine functions present in the $Ar'_1$ group of compound (III) are salified or protected beforehand.

The compounds of formula (II) are prepared by following the procedure described in European patent 790 997 and U.S. Pat. No. 5,733,913, as described in scheme 1 below:

SCHEME 1

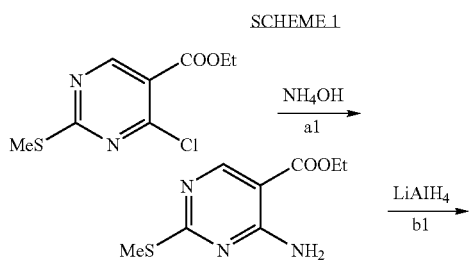

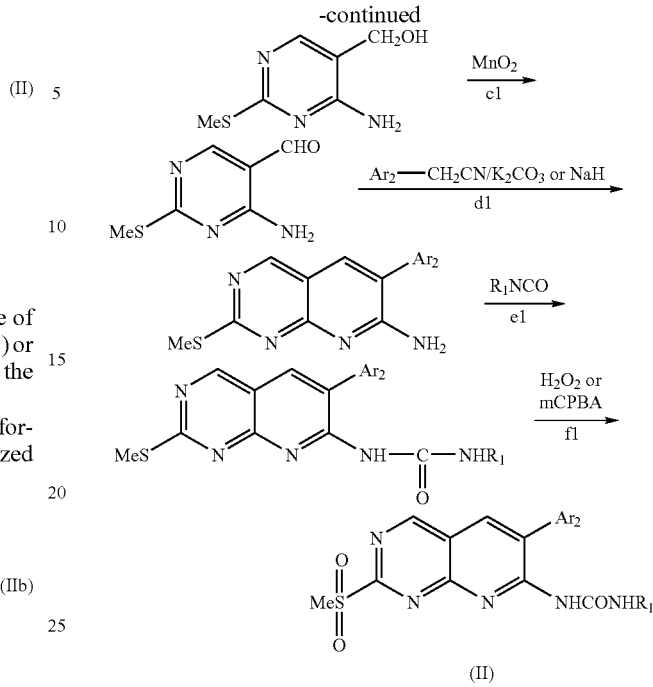

mCPBA: meta-chloroperbenzoic acid.

The amines of formula (III) $Ar'_1NH2$ are known or prepared by known methods from the corresponding nitrated derivatives $Ar'_1NO_2$ (IV), by reduction either (i) in an acidic medium in the presence of a metal such as powdered zinc or iron, or (ii) by hydrogen in the presence of a catalyst such as Pd/C. Ar' is Ar or a precursor of Ar.

The compounds of formula (IV) are known or prepared by known methods.

The compounds according to the invention are obtained in racemic form; the optically pure isomers can then be prepared using resolving methods known to those skilled in the art, such as crystallization by formation of salts with chiral agents. Compounds according to the invention in optically pure form can also be prepared using methods of asymmetric or stereospecific synthesis, the use of chromatographic techniques using a chiral phase. Moreover, the products of the invention can be separated via the formation of diastereoisomers, separation thereof, and then the decomposition of the pharmaceutically useful diastereoisomer into its enantiomerically pure active product. Enzymatic techniques can also be used. Additional known separating techniques can be used. They include those disclosed in: Enantiomers, Racemates, and Resolutions, John Wiley and Sons, New York (1981).

The compounds according to the invention can also be prepared in a form enriched in one stereoisomer as soon as there is preparation of the synthesis intermediates. Thus, the resolving of the enantiomers of the amines of formula (III) or of the nitrated precursors (IV) can be carried out by one of the abovementioned methods.

The following examples describe the preparation of certain intermediates and of compounds in accordance with the invention. These examples are not limiting and merely illustrate the present invention.

In the examples, the following abbreviations are used:
Boc: tert-butoxycarbonyl
BOP: benzotriazol-1-yloxytris(dimethylamino)phosphonium hexafluorophosphate
THF: tetrahydrofuran
AT: ambient temperature
TFA: trifluoroacetic acid
DCM: dichloromethane
DMSO: dimethyl sulphoxide
DMF: dimethylformamide
MeOH: methanol
DCCI: dicyclohexylcarbodiimide
DIPEA: diisopropylethylamine
$KHSO_4/K_2SO_4$: 5% solution of $KHSO_4/K_2SO_4$.

The proton nuclear magnetic resonance (NMR) spectra are recorded at 200 or 250 MHz in DMSO-$d_6$, unless otherwise indicated. The DMSO-$d_6$ signal is at 2.5 ppm and serves as a reference. For the interpretation of the spectra, the following abbreviations are used: s: singlet, d: doublet, t: triplet, m: unresolved peak, mt: multiplet, bs: broad singlet, dd: doublet of a doublet, qd: quadruplet, qt: quintuplet.

Mp: melting point (in degrees Celsius) as measured on a Büchi B545 apparatus with a temperature gradient of 1° C. per minute.

MH+: Mass spectrum. The compounds are analyzed by HPLC—UV—MS (liquid chromatography—UV detection—mass spectrometry) coupling. The device used, sold by Agilent, is composed of an HP1100 chromatograph equipped with an Agilent diode array detector and an MSD Quad quadripolar mass spectrometer.

The analytical conditions are as follows:

Column: C 18 Symmetry (50×2.1 mm; 3.5 µm)
Eluent A: $H_2O$+0.005% TFA at pH 3.15
Eluent B: $CH_3CN$+0.005% TFA
Gradient:

| Time (min) | % B |
|---|---|
| 0 | 0 |
| 10 | 90 |
| 15 | 90 |
| 16 | 0 |
| 20 | 0 |

Column temperature: 30° C.
Flow rate: 0.4 ml/min
Detection: λ = 210 nm
tr: retention time
v: volume.

Preparation of a Compound of Formula (II)
Preparation 1

N-(t-Butyl)-N'-[6-(2,6-dichlorophenyl)-2-(methylsulphonyl)pyrido[2,3-d]pyrimidin-7-yl]urea

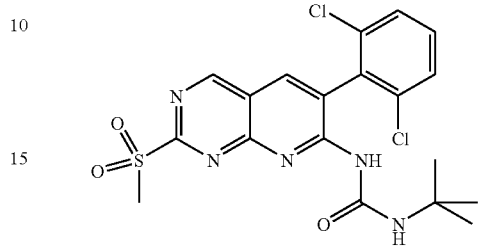

1.1 Ethyl
4-amino-2-(methylthio)pyrimidine-5-carboxylate 140 ml of a 20% $NH_4OH$ solution are added, in 20 minutes, and while maintaining the temperature at around 20° C., to a suspension of 50.7 g of ethyl 4-chloro-2-(methylthio)pyrimidin-5-carboxylate in 400 ml of EtOH. After stirring at ambient temperature for 20 hours, the reaction medium is concentrated under vacuum almost to dryness, and the residue is then taken up in 350 ml of water, stirred for 20 minutes, filtered, washed with 3×60 ml of water, and then dried under vacuum in the presence of $P_2O_5$. A white solid is obtained, Mp=134-135° C., m=39.9 g.

1.2
[4-Amino-2-(methylthio)pyrimidin-5-yl]methanol 210 ml of a 1M solution of $LiAlH_4$ in THF are added, in 45 minutes, while maintaining the temperature below 30° C., to 39.68 g of ester obtained in the previous stage dissolved in 1 litre of THF. The mixture is stirred for a further hour and the temperature is then decreased to 5° C. and 9 ml of water, 6.5 ml of 5N sodium hydroxide and then 32 ml of water are successively added dropwise. After stirring for 10 minutes, the solid is filtered off and then rinsed with THF. The filtrate is concentrated to dryness under vacuum and the residue is then redissolved in 600 ml of boiling toluene, the product is rapidly filtered under hot conditions in order to remove some of the insoluble material and the filtrate is left to cool overnight. The white crystals obtained are filtered, washed with a small amount of toluene and then of ether and dried, Mp=124-127° C., m=23.9 g.

1.3
4-Amino-2-(methylthio)pyrimidine-5-carbaldehyde 79.5 g of active $MnO_2$ are added, in 2 minutes, to a suspension of 23.8 g of the alcohol obtained in the previous stage in 1600 ml of chloroform, and the mixture is stirred at ambient temperature overnight; the solid is filtered off, and washed with 3×75 ml of $CHCl_3$, and the filtrate is concentrated to dryness under vacuum; the white solid residue is taken up in ether, filtered and dried, Mp=184-186° C., m=21.05 g.

1.4 6-(2,6-Dichlorophenyl)-2-(methylthio)pyrido[2,3-d]pyrimidin-7-amine 5.47 g of 60% NaH are added, in 5 minutes, to 21 g of the aldehyde obtained in the previous stage, dissolved in 240 ml of DMF and cooled to 5° C., followed by 29.05 g of 2,6-dichlorophenylacetonitrile, in 20 minutes, in small fractions. The stirring is continued for 30 minutes at 5° C. and then at ambient temperature overnight. The reaction medium is cooled to 5° C. and 65 ml of a saturated NH$_4$Cl solution and then 500 ml of a water/ice mixture are added; a red precipitate forms, which is filtered off, washed twice with water, filter-dried to a maximum, and washed with ether, with 100 ml of chloroform and then with ether again; after drying, a beige solid is obtained, Mp=250-253° C., m=29.92 g.

The ether and chloroform washing phases are concentrated to dryness, and the product is taken up in a small amount of chloroform, to which ether is added: a second cast of 3.15 g is obtained, total m=33.07 g.

1.5 N-(t-Butyl)-N'-[6-(2,6-dichlorophenyl)-2-(methylthio)pyrido[2,3-d]pyrimidin-7-yl]urea 4.6 g of 60% NaH are added, in 10 minutes and while maintaining the temperature below 25° C., to 29.9 g of the amine obtained above in solution in 300 ml of DMF; the mixture is stirred for a further 20 minutes and then 12.2 ml of tert-butyl isocyanate are added in 20 minutes and the mixture is stirred overnight. The reaction medium is poured slowly onto 800 ml of a water/ice mixture+100 ml of 6N HCl; the precipitate formed is filtered, washed with water, filter-dried, and then stirred for 1 hour in 300 ml of ether, then filtered, washed with ether and dried. A beige solid is obtained, Mp=195-196° C. (decomp.), m=26.5 g.

1.6 N-(t-Butyl)-N'-[6-(2,6-dichlorophenyl)-2-(methylsulphonyl)pyrido[2,3-d]pyrimidin-7-yl]urea 27 g of meta-chloroperbenzoic acid (77%) are added, in 25 minutes and while maintaining the temperature below 25° C., to 21.95 g of urea obtained above in solution in 300 ml of chloroform. A precipitate forms. After 2 hours, the reaction medium is diluted with 1 litre of dichloromethane and Na$_2$SO$_4$ followed by 14 g of Ca(OH)$_2$ are added. After stirring for 30 minutes, the solid is filtered off and washed with dichloromethane and the filtrate is then concentrated to dryness. The residue is triturated in 80 ml of ether under hot conditions; the product is left to cool, and the white solid is then filtered off, washed with ether and dried, Mp=138-140° C., m=20.5 g.

In the same manner as for the compound described in preparation 1, the compounds of formula (II) below can be prepared:

TABLE 1

| Prep. | Ar2 | R1 | NMR |
|---|---|---|---|
| 1 | 2,6-dichlorophenyl | tert-butyl | 1.40: s: 9H; 3.50: s: 3H; 7.50-7.70: m: 3H; 8.55: s: 1H; 9.10: s: 1H; 9.60: s: 1H; 9.95: s: 1H. |
| 2 | 2,6-dichlorophenyl | phenyl | 3.50 ppm: s: 3H; 7.10 ppm: t: 1H; 7.40 ppm: t: 2H; 7.55-7.75 ppm: m: 5H; 8.60 ppm: s: 1H; 9.60 ppm: s: 1H; 9.80 ppm: s: 1H; 11.90 ppm: s: 1H. |
| 3 | 3,5-dimethoxyphenyl | tert-butyl | 1.40 ppm: s: 9H; 3.50 ppm: s: 3H; 3.80 ppm: s: 6H; 6.65-6.80 ppm: mt: 3H; 7.75 ppm: s: 1H; 8.45 ppm: s: 1H; 9.60 ppm: s: 1H; 9.80 ppm: s: 1H. |
| 4 | 2,6-dichlorophenyl | ethyl | 1.20 ppm: t: 3H; 3.40 ppm: qd: 2H; 3.50 ppm: s: 3H; 7.50 ppm-7.75 ppm: m: 3H; 8.55 ppm: s: 1H; 9.40 ppm: s: 1H; 9.60 ppm: s: 1H; 9.70 ppm: s: 1H. |
| 5 | 3,4-dimethoxyphenyl | tert-butyl | 1.40 ppm: s: 9H; 3.45 ppm: s: 3H; 3.80 ppm: s: 3H; 3.90 ppm: s: 3H; 7.10-7.20 ppm: m: 3H; 7.75 ppm: s: 1H; 8.45 ppm: s: 1H; 9.55 ppm: s: 1H; 9.80 ppm: s: 1H. |
| 6 | phenyl | tert-butyl | 1.40 ppm: s: 9H; 3.50 ppm: s: 3H; 7.60 ppm: bs: 6H; 8.45 ppm: s: 1H; 9.40 ppm: s: 1H; 9.80 ppm: s: 1H. |
| 7 | 2-methoxyphenyl | tert-butyl | 1.40 ppm: s: 9H; 3.50 ppm: s: 3H; 3.80 ppm: s: 3H; 7.10-7.40 ppm: mt: 4H; 7.60 ppm: t: 1H; 8.40 ppm: s: 1H; 9.60 ppm: s: 1H; 9.80 ppm: s: 1H. |
| 8 | 2,6-dibromophenyl | tert-butyl | 1.40 ppm: s: 9H; 3.50 ppm: s: 3H; 7.40 ppm: t: 1H; 7.85 ppm: d: 2H; 8.50 ppm: s: 1H; 9.00 ppm: s: 1H; 9.60 ppm: s: 1H; 10.00 ppm: s: 1H. |
| 9 | 2-bromo-6-chlorophenyl | tert-butyl | 1.40 ppm: s: 9H; 3.45 ppm: s: 3H; 7.50 ppm: t: 1H; 7.65 ppm: d: 1H; 7.80 ppm: d: 1H; 8.50 ppm: s: 1H; 9.00 ppm: s: 1H; 9.50 ppm: s: 1H; 9.90 ppm: s: 1H. |
| 10 | 2,6-dibromophenyl | ethyl | 1.15 ppm: t: 3H; 3.30 ppm: qd: 2H (masked by DOH); 3.50 ppm: s: 3H; 7.40 ppm: t: 1H; 7.85 ppm: d: 2H; 8.50 ppm: s: 1H; 9.25 ppm: s: 1H; 9.60 ppm: s: 1H; 9.70 ppm: s: 1H. |
| 11 | 2-bromo-6-chlorophenyl | phenyl | (DMSO + TFA) 3.55 ppm: s: 3H; 7.10 ppm: t: 1H; 7.30-7.90 ppm: m: 7H; 8.60 ppm: s: 1H; 9.65 ppm: s: 1H. |
| 12 | 2,6-dibromophenyl | phenyl | 3.55 ppm: s: 3H; 7.10 ppm: t: 1H; 7.35 ppm: qd: 3H; 7.60 ppm: d: 2H; 7.85 ppm: d: 2H; 8.60 ppm: s: 1H; 9.70 ppm: s: 1H; 9.80 ppm: s: 1H; 12.00 ppm: s: 1H. |
| 13 | 2,4-dichlorophenyl | tert-butyl | 1.35 ppm: s: 9H; 3.50 ppm: s: 3H; 7.45-7.60 ppm: mt: 2H; 7.80 ppm: s: 1H; 8.40 ppm: s: 1H; 8.80 ppm: s: 1H; 9.55 ppm: s: 1H; 9.80 ppm: s: 1H. |
| 14 | 2,6-dimethylphenyl | tert-butyl | 1.40 ppm: s: 9H; 2.00 ppm: s: 6H; 3.50 ppm: s: 3H; 7.10 ppm: s: 1H; 7.25-7.45: m: 3H; 8.45 ppm: s: 1H; 9.60 ppm: s: 1H; 9.80 ppm: s: 1H. |
| 15 | 2,6-difluorophenyl | tert-butyl | 1.40 ppm: s: 9H; 3.50 ppm: s: 3H; 7.25-7.40: mt: 2H; 7.55-7.70 ppm: mt: 1H; 8.65 ppm: s: 1H; 9.20 ppm: s: 1H; 9.60 ppm: s: 1H; 9.75 ppm: s: 1H. |
| 16 | 2,6-dichlorophenyl | isopropyl | 1.20 ppm: d: 6H; 3.50 ppm: s: 3H; 3.85-4.00 ppm: mt: 1H; 7.50-7.70 ppm: m: 3H; 8.50 ppm: s: 1H; 9.25 ppm: s: 1H; 9.65 ppm: s: 1H; 9.75 ppm: bs: 1H. |

Preparation of the Compounds of Formula (III)

The preparation numbers used refer to the numbers of the compounds in Table 2 hereinafter.

Preparations 17 and 18 Commercial product.

Preparation 19 Prepared according to *J. Hetero. Chem.* 1986, 23, 1645-1649 and isolated in hydrochloride form.

Preparation 20

Prepared according to *J. Chem. Soc.* 1928, 121.

Preparation 21

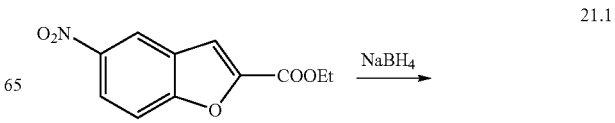

21.1

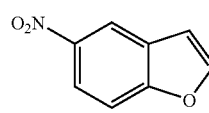

2.27 g of NaBH$_4$ are added, in small portions over a period of 8 hours, to 1.12 g of ethyl 5-nitrobenzo[b]furan-2-carboxylate in 50 ml of THF, and the mixture is then stirred for 40 hours. 5 ml of methanol and then 5 ml of water are added. The reaction medium is extracted with EtOAc, and the organic phase is washed with water, with a 5% KHSO$_4$/K$_2$SO$_4$ solution, with water, and then with a saturated NaCl solution. After drying and concentration under reduced pressure, 0.74 g of the expected product are recovered in solid form.

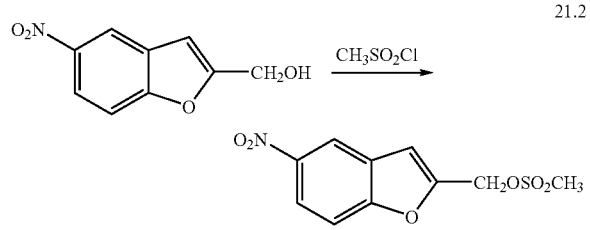

730 mg of the product obtained in stage 21.1 are dissolved in 9 ml of DCM and maintained at 5° C. 1 ml of triethylamine is added at 5° C., and then 536 mg of methanesulphonyl chloride are added in 15 minutes. The temperature is maintained at 5° C. for 15 minutes, and the reaction medium is then allowed to return to ambient temperature for 55 minutes. The reaction medium is then diluted with DCM and water. The organic phase is separated by settling out, washed with water and with a saturated NaCl solution, dried and evaporated under reduced pressure. 0.98 g of oil, comprising a mixture of mesylate (expected product) and of chloride (product from substitution of the CH$_2$OH in the 2-position of benzo[b]furan with CH$_2$Cl), is obtained.

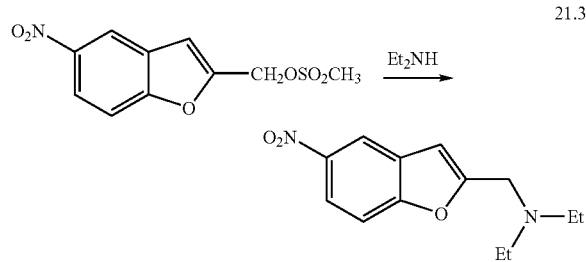

0.97 g of the product obtained in stage 21.2, in 10 ml of DMF, are treated with 1.05 g of diethylamine for 18 hours. The reaction medium is extracted with EtOAc, the organic phase is washed with water and with a saturated NaCl solution and dried, and the solvents are then evaporated off under reduced pressure. 0.93 g of oil is obtained.

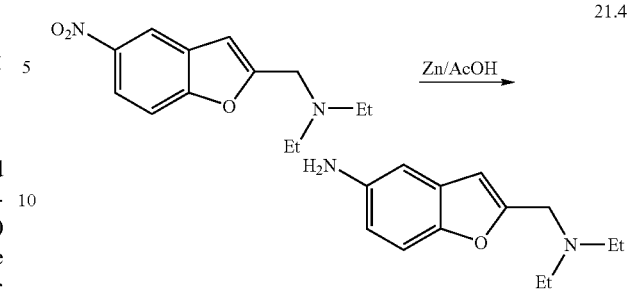

4.48 g of powdered Zn are added to 1.16 g of product obtained in stage 21.3 in 40 ml of THF, followed, at −5° C., by 5 ml of acetic acid, over a period of 25 minutes.

After 1 h 15 of reaction, the residual solid is eliminated from the reaction medium by filtration, the solid is washed with a small amount of THF, and the organic phases are combined, diluted with EtOAc and water, and then brought to pH=9 with 10N NaOH. After separation by settling out, the organic phase is isolated and washed with a 15% Na$_2$CO$_3$ solution, with water and with a saturated NaCl solution, dried and evaporated. 900 mg of oil are obtained.

Preparation 22

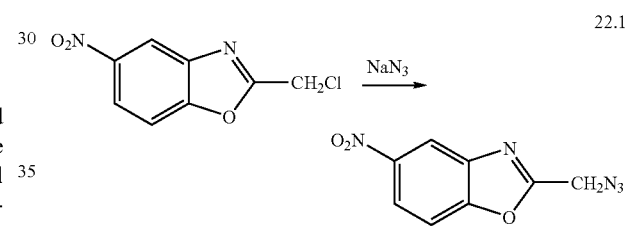

1.26 g of sodium azide are added to 1.64 g of 2-chloromethyl-5-nitrobenzoxazole (prepared according to *Synth. Communications* 1989, 19, 2921-2924) in 25 ml of DMF and the mixture is stirred at ambient temperature overnight. The reaction medium is poured onto 150 ml of EtOAc and washed twice with ice-cold water and then with a saturated NaCl solution. The organic phase is dried and concentrated under reduced pressure. 1.42 g of black oil are recovered.

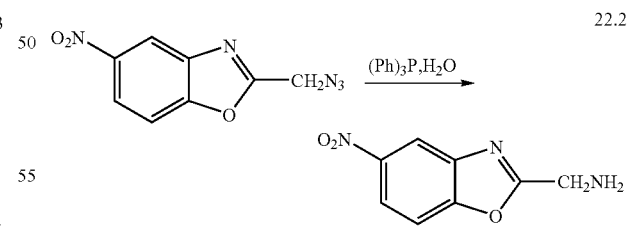

2.84 g of triphenylphosphine are added, in 10 minutes to 1.40 g of the product obtained in stage 22.1 in 30 ml of EtOAc, and then, after 10 minutes, 1.16 ml of water are added in 2 minutes. After 24 hours with stirring at 60° C., and then cooling, the reaction medium is diluted with EtOAc, and the organic phase is washed with water and then with a saturated NaCl solution. The organic phase is dried and concentrated under reduced pressure. The residue is taken up in Et$_2$O and is extracted twice with 1N HCl. The acid phases are combined, brought into contact with EtOAc, and brought to pH=10 with 10N NaOH. After separation by settling out, the organic phase is washed with water and then with a saturated NaCl solution. The organic phase is dried and concentrated under reduced pressure, to give 468 mg of the expected product in the form of an oil.

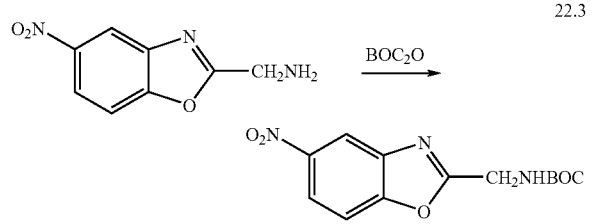

22.3

The product obtained in stage 22.2 is dissolved in 10 ml of DCM, and then 0.4 equivalent of triethylamine followed by 1.1 equivalents of $BOC_2O$ are added. After 5 h, the reaction medium is diluted with $CH_2Cl_2$ and then washed successively with a 5% $KHSO_4/K_2SO_4$ solution, water and a saturated NaCl solution. The crude is dried and evaporated under reduced pressure, so as to obtain 388 mg of the expected product.

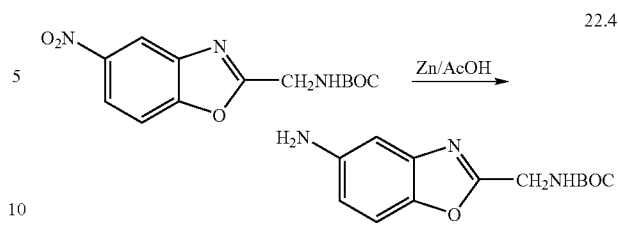

22.4

The product obtained in stage 19.3 is reduced quantitatively with Zn/AcOH, so as to obtain an oil, according to the method described in preparation 18.4.

Preparation 23

23.1 Prepared according to *J. Hetero. Chem.* 1973, 10, 755.

23.2 Reduction of the product obtained in stage 23.1 with Sn/HBr in water according to *Chem.Abstr.* 1950, 4474.

Preparation 24 Prepared according to *J. Hetero. Chem.* 1970, 7, 1019-1027.

Preparation 25 Prepared according to *Boll. Sci. Fac. Chim. Ind. Bologna* 1964 vol. 22 pages 33-37

Preparation 26

Prepared according to the procedure described in patent application WO92/05164.

The compounds of formula (III) are characterized in Table 2 below:

TABLE 2

Preparations of the compounds of formula (III).

| Prep. | $Ar_1$ | $X = NO_2$ (IV), HCl NMR | $X = NH_2$ (III) NMR |
|---|---|---|---|
| 17 | benzothiadiazole structure with X | — | Commercial product |
| 18 | benzothiadiazole structure with X | — | Commercial product |
| 19 | benzisothiazole SO₂/NH with X | — | Prepared according to J. Hetero. Chem. 1986, 23, 1645-1649 and isolated in hydrochloride form |
| 20 | benzoxazole-2-Me with X | — | Prepared according to J. Chem. Soc. 1928, 121 |
| 21 | benzofuran-CH₂-N(Et)₂ with X | 21.3 1.00 ppm: t: 6 H; 2.50 ppm: qd: 4 H; 3.75 ppm: s: 2 H; 7.00 ppm: s: 1 H; 7.75 ppm: d: 1 H; 8.15 ppm: d: 1 H; 8.50 ppm: d: 1 H. | 21.4 1.00 ppm: t: 6 H; 2.55 ppm: qd: 4 H; 3.65 ppm: s: 2 H; 4.90 ppm: bs: 2 H; 6.45 ppm: s: 1 H; 6.50 ppm: dd: 1 H; 6.65 ppm: d: 1 H; 7.15 ppm: d: 1 H. |

TABLE 2-continued

Preparations of the compounds of formula (III).

| Prep. | Ar₁ | X = NO₂ (IV), HCl NMR | X = NH₂ (III) NMR |
|---|---|---|---|
| 22 | (benzoxazole with CH₂-NHBOC substituent) | 22.3 1.40 ppm: s: 9 H; 4.45 ppm: d: 2 H; 7.65 ppm: t: 1 H; 7.95 ppm: d: 1 H; 8.30 ppm: dd: 1 H; 8.60 ppm: d: 1 H. | 22.4 1.35 ppm: s: 9 H; 4.25 ppm: d: 2 H; 4.95: bs: 2 H; 6.55 ppm: dd: 1 H; 6.75 ppm: d: 1 H; 7.25 ppm: d: 1 H; 7.45 ppm: t: 1 H. |
| 23 | (imidazo[1,2-a]pyridine) | 23.1 Prepared according to J. Hetero. Chem. 1973, 10, 755 | 23.2 Prepared according to Chem. Abstr. 1950, 4474. |
| 24 | (triazolopyridine) | — | Prepared according to J. Hetero. Chem. 1970, 7, 1019-1027 |
| 25 | (benzoxadiazole) | — | Prepared according to Boll. Sci. Fac. Chim. Ind. Bologna 1964 vol. 22 pages 33-37 |
| 26 | (benzisothiazole dioxide) | — | Prepared according to the procedure described in patent application WO92/05164 |

The numbers of the compounds exemplified refer to those given in Table 3 hereinafter, which illustrates the chemical structures and the physical properties of some compounds according to the invention. When they contain an asymmetrical carbon, these compounds are obtained in racemic form.

EXAMPLE 1

(Compound No. 1) N-[2-(2,1,3-benzothiadiazol-5-ylamino)-6-(2,6-dichlorophenyl)pyrido[2,3-d]pyrimidin-7-yl]-N'-(1,1-dimethylethyl)urea 3.21 g (28.6 mmol) of t-BuOK are added, in 15 minutes, to 3.32 g (20 mmol) of the amine of preparation 17 in Table 2, in 45 ml of DMSO, and then 7.71 g (16.5 mmol) of the urea of preparation 1 in Table 1 are added in 20 minutes. 1 g of t-BuOK is again added after 2 hours, and then 1 g of t-BuOK is again added after 2 hours. After reaction for 6 hours, the reaction medium is diluted with ice-cold water, and then extracted with EtOAc. The organic phase is washed twice with water and once with a saturated NaCl solution, dried and concentrated under reduced pressure. The crude is triturated in an Et₂O/heptane mixture, and the precipitate is filtered off and then chromatographed on silica gel, the eluent being 88/12 (v/v) CHCl₃/EtOAc. 5 g of expected product are obtained. MH⁺=539.

EXAMPLE 2

(Compound No. 2) N-[2-(2,1,3-benzothiadiazol-4-ylamino)-6-(2,6-dichlorophenyl)pyrido[2,3-d]pyrimidin-7-yl]-N'-(1,1-dimethylethyl)urea Compound 2 is prepared in the same way as compound 1, starting with the amine of preparation 18 in Table 2.

EXAMPLE 3

(Compound No. 3) N-[6-(2,6-dichlorophenyl)-2-[(1,3-dihydro-2,2-dioxido-2,1-benzisothiazol-5-yl)amino]pyrido[2,3-d]pyrimidin-7-yl]-N'-(1,1-dimethylethyl)urea A mixture of 437 mg of the amine of preparation 19 in Table 2, in hydrochloride form, and of 750 mg of the urea of preparation 1 in Table 1, are heated in 15 ml of ethanol for 5 hours. The reaction medium is evaporated to dryness and then taken up in 50 ml of CHCl₃ and 20 ml of a saturated NaHCO₃ solution. The organic phase is separated by settling out, and washed with water and then with a saturated NaCl solution. The organic phase is dried and saturated under reduced pressure. The residue is purified by flash chromatography with a gradient of 0 to 20% (v/v) of EtOAc in chloroform. 275 mg of a yellow solid are obtained. MH⁺: 572.

EXAMPLE 4

(Compound No. 4) N-[6-(2,6-dichlorophenyl)-2-[(2-methyl-6-benzoxazolyl)amino]pyrido[2,3-d]pyrimidin-7-yl]-N'-(1,1-dimethylethyl)urea 210 mg of the amine of preparation 20 in Table 2 and 562 mg of the urea of preparation 1 in Table 1 are heated for 8 hours at 45° C. in 20 ml of ethanol containing 0.02 ml of concentrated HCl. After concentration under reduced pressure, the residue is chromatographed on silica gel, the eluent being CHCl$_3$/MeOH: 98/2 (v/v). 300 mg of product in the form of a yellow solid are isolated. MH$^+$: 536.

EXAMPLE 5

(Compound No. 5) N-[6-(2,6-dichlorophenyl)-2-[[2-[(diethylamino)methyl]-5-benzofuranyl]amino]pyrido[2,3-d]pyrimidin-7-yl]-N'-(1,1-dimethylethyl)urea Compound 5 is prepared in the same way as compound 4, starting from the amine 21.4 of preparation 21 in Table 2.

EXAMPLE 6

Compound No. 6 1,1-dimethylethyl [[5-[[6-(2,6-dichlorophenyl)-7-[[[(1,1-dimethylethyl)amino]carbonyl]amino]pyrido[2,3-d]pyrimidin-2-yl]amino]-2-benzoxazolyl]methyl]carbamate Compound 6 is prepared in the same way as compound 4, starting from the amine 22.4 of preparation 22 in Table 2.

EXAMPLE 7

(Compound No. 7) N-[2-[[2-(aminomethyl)-5-benzoxazolyl]amino]-6-(2,6-dichlorophenyl)pyrido[2,3-d]pyrimidin-7-yl]-N'-(1,1-dimethylethyl)urea 190 mg of compound 6 are treated for 1 hour with 3 ml of TFA in 2 ml of DCM. After concentration under reduced pressure, the residue is taken up in a DCM/water mixture and the pH is then brought to 9 by adding a 15% Na$_2$CO$_3$ solution. After separation by settling out, the organic phase is washed with water and then with a saturated NaCl solution, dried, and concentrated under reduced pressure. The crude is purified by flash chromatography on silica gel, the eluant being 0 to 10% (v/v) of methanol in DCM. 100 mg of yellow solid are isolated. MH$^+$: 551.

EXAMPLE 8

(Compound No. 8) N-[6-(2,6-dichlorophenyl)-2-(imidazo[1,2-a]pyridin-6-ylamino)pyrido[2,3-d]pyrimidin-7-yl]-N'-(1,1-dimethylethyl)urea Compound 8 is prepared in the same way as compound 4, starting from the amine 23.2 of preparation 23 in Table 2.

EXAMPLE 9

(Compound No. 9) N-[6-(2,6-dichlorophenyl)-2-([1,2,4]triazolo[1,5-a]pyridin-6-ylamino)pyrido[2,3-d]pyrimidin-7-yl]-N'-(1,1-dimethylethyl)urea Compound 9 is prepared in the same way as compound 4, starting from the amine of preparation 24 in Table 2.

EXAMPLE 10

(Compound No. 10) N-[2-(2,1,3-benzoxadiazol-5-ylamino)-6-(2,6-dichlorophenyl)pyrido[2,3-d]pyrimidin-7-yl]-N'-(1,1-dimethylethyl)urea 0.168 g of tBuOK is added in 25 minutes, to a mixture of 0.468 g of the product of preparation 1 and 0.202 g of the amine (III) of preparation 25 in Table 2, in 6 ml of DMSO, and then a further 0.168 g is added in 1 hour. After stirring for 2 hours, the reaction medium is extracted with ethyl acetate which is washed successively with water and a saturated NaCl solution. After drying over Na$_2$SO$_4$ and evaporation of the ethyl acetate, the crude product is purified by flash chromatography on silica gel with a gradient of 0 to 8% (v/v) of ethyl acetate in dichloromethane. A beige powder is obtained, m=0.22 g. MH+=523.

EXAMPLE 11

(Compound No. 11) N-[2-(1,3-dihydro-2,2-dioxido-2,1,3-benzothiadiazol-5-ylamino)-6-(2,6-dichlorophenyl)pyrido[2,3-d]pyrimidin-7-yl]-N'-(1,1-dimethylethyl)urea Compound 11 is prepared in the same way as compound 4, starting from the amine of preparation 26 in Table 2.

EXAMPLES 12-21

Compounds No. 12-21

Compounds 12-21 are prepared in the same way as compound 1, starting from the amine (III) of preparation 17 in Table 2 and an appropriate urea selected from the products of formula (II) of the preparations in Table 1.

EXAMPLE 12

(Compound No. 12) N-[2-(2,1,3-benzothiadiazol-5-ylamino)-6-(2-bromo-6-chlorophenyl)pyrido[2,3-d]pyrimidin-7-yl]-N'-(1,1-dimethylethyl)urea

EXAMPLE 13

(Compound No. 13) N-[2-(2,1,3-benzothiadiazol-5-ylamino)-6-(2,6-dichlorophenyl)pyrido[2,3-d]pyrimidin-7-yl]-N'-ethylurea

EXAMPLE 14

(Compound No. 14) N-[2-(2,1,3-benzothiadiazol-5-ylamino)-6-(2,6-dibromophenyl)pyrido[2,3-d]pyrimidin-7-yl]-N'-(1,1-dimethylethyl)urea

EXAMPLE 15

(Compound No. 15) N-[2-(2,1,3-benzothiadiazol-5-ylamino)-6-(2,6-dibromophenyl)pyrido[2,3-d]pyrimidin-7-yl]-N'-ethylurea

EXAMPLE 16

(Compound No. 16) N-[2-(2,1,3-benzothiadiazol-5-ylamino)-6-(2,6-dichlorophenyl)pyrido[2,3-d]pyrimidin-7-yl]-N'-phenylurea

EXAMPLE 17

(Compound No. 17) N-[2-(2,1,3-benzothiadiazol-5-ylamino)-6-(3,5-dimethoxyphenyl)pyrido[2,3-d]pyrimidin-7-yl]-N'-(1,1-dimethylethyl)urea

EXAMPLE 18

(Compound No. 18) N-[2-(2,1,3-benzothiadiazol-5-ylamino)-6-phenylpyrido[2,3-d]pyrimidin-7-yl]-N'-(1,1-dimethylethyl)urea

EXAMPLE 19

(Compound No. 19) N-[2-(2,1,3-benzothiadiazol-5-ylamino)-6-(2,6-dimethylphenyl)pyrido[2,3-d]pyrimidin-7-yl]-N'-(1,1-dimethylethyl)urea

EXAMPLE 20

(Compound No. 20) N-[2-(2,1,3-benzothiadiazol-5-ylamino)-6-(2,6-difluorophenyl)pyrido[2,3-d]pyrimidin-7-yl]-N'-(1,1-dimethylethyl)urea

EXAMPLE 21

(Compound No. 21) N-[2-(2,1,3-benzothiadiazol-5-ylamino)-6-(2,6-dichlorophenyl)pyrido[2,3-d]pyrimidin-7-yl]-N'-(1-methylethyl)urea Tables 3 and 4 below illustrate the chemical structures and the physical properties of some examples according to the invention. In these tables, Me, Et, iPr and tBu are, respectively, methyl, ethyl, isopropyl and tert-butyl groups, and Boc (or BOC) is the tert-butoxycarbonyl group.

TABLE 3

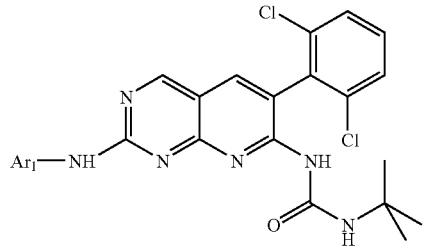

(I)

| Compounds | Ar₁ | NMR characterization |
|---|---|---|
| 1 | 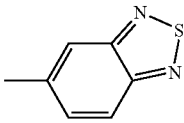 | 1.50 ppm: s: 9 H; 7.50-7.70 ppm: m: 3 H; 7.95 ppm: dd: 2 H; 8.15 ppm: s: 1 H; 8.35 ppm: s: 1 H; 9.20 ppm: s: 1 H; 9.35 pmm: s: 1 H; 10.65 ppm: s: 1 H; 10.75 ppm: s: 1 H. |
| 2 | 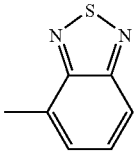 | 1.40 ppm: s: 9 H; 7.45-7.80 ppm: m: 5 H; 8.15 ppm: s: 1 H; 8.35 ppm: s: 1 H; 8.80 ppm: d: 1 H; 9.20 ppm: s: 1 H; 9.55 pmm: s: 1 H; 10.60 ppm: s: 1 H. |
| 3 | 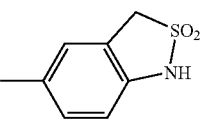 | 1.45 ppm: s: 9 H; 4.45 ppm: s: 2 H; 6.75 ppm: d: 1 H; 7.45-7.70 ppm: m: 3 H; 7.80 ppm: de: 1 H; 8.05 ppm: s: 1 H; 8.15 ppm: bs: 2 H; 9.05 ppm: s: 1 H; 10.10 ppm: s: 1 H; 10.20-10.30 ppm: bs: 1 H; 10.60 ppm: s: 1 H. |
| 4 | 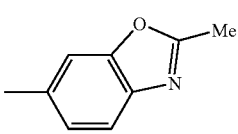 | 1.45 ppm: s: 9 H; 2.60 ppm: s: 3 H; 7.50-7.70 ppm: m: 5 H; 8.10 ppm: s: 1 H; 8.30 ppm: bs: 1 H; 8.90 ppm: bs: 1 H; 9.15 ppm: s: 1 H; 10.45 ppm: s: 1 H; 10.75 ppm: s: 1 H. |

TABLE 3-continued (I)

| Compounds | Ar₁ | NMR characterization |
|---|---|---|
| 5 | 5-methyl-benzofuran-2-yl-CH₂-N(Et)(Et) | 1.00 ppm: t: 6 H; 1.45 ppm: s: 9 H; 2.50 ppm: qd: 4 H; 3.70 ppm: s: 2 H; 6.55 ppm: s: 1 H; 7.40-7.70 ppm: m: 5 H; 8.10 ppm: s: 2 H; 8.55 ppm: bs: 1 H; 9.10 ppm: s: 1 H; 10.15 ppm: s: 1 H; 10.65 ppm: s: 1 H. |
| 6 | 5-methyl-benzoxazol-2-yl-CH₂-NHBOC | 1.30 ppm: s: 9 H; 1.40 ppm: s: 9 H; 4.35 ppm: d: 2 H; 7.45-7.60 ppm: m: 5 H; 7.75 ppm: dd: 1 H; 8.05 ppm: s: 1 H; 8.10 ppm: bs: 1 H; 8.65 ppm: s: 1 H; 9.10 ppm: s: 1 H; 10.30 ppm: s: 1 H; 10.60 ppm: s: 1 H. |
| 7 | 5-methyl-benzoxazol-2-yl-CH₂-NH₂ | 1.45 ppm: s: 9 H; 2.10 ppm: bs: 2 H; 3.90 ppm: s: 2 H; 7.45-7.70 ppm: m: 4 H; 7.80 ppm: dd: 1 H; 8.05 ppm: s: 1 H; 8.15 ppm: bs: 1 H; 8.65 ppm: s: 1 H; 9.10 ppm: s: 1 H; 10.25 ppm: s: 1 H; 10.70 ppm: s: 1 H. |
| 8 | 6-methyl-imidazo[1,2-a]pyridin-2-yl | 1.50 ppm: s: 9 H; 7.40-7.70 ppm: m: 7 H; 8.10 ppm: s: 1 H; 8.20 ppm: s: 1 H; 9.10 ppm: s: 1 H; 9.65 ppm: s: 1 H; 10.30 ppm: s: 1 H; 10.60 ppm: s: 1 H. |
| 9 | 6-methyl-[1,2,4]triazolo[1,5-a]pyridin-2-yl | 1.50 ppm: s: 9 H; 7.45-7.70 ppm: m: 3 H; 7.85 ppm: s: 2 H; 8.15 ppm: s: 1 H; 8.25 ppm: d: 1 H; 8.40 ppm: s: 1 H; 9.15 ppm: s: 1 H; 10.10 pmm: s: 1 H; 10.55 ppm: s: 1 H; 10.60 ppm: s: 1 H. |
| 10 | 5-methyl-benzo[c][1,2,5]oxadiazol-yl | 1.45 ppm: s: 9 H; 7.50-7.70 ppm: mt: 3 H; 7.75 ppm: d: 1 H; 8.00 ppm: d: 1 H; 8.20 ppm: s: 1 H; 8.40 ppm: s: 1 H; 9.15 ppm: s: 1 H; 9.25 ppm: s: 1 H; 10.65 ppm: s: 1 H; 10.90 ppm: s: 1 H. |
| 11 | 5-methyl-2,1,3-benzothiadiazole-1,1-dioxide | 1.45 ppm: s: 9 H; 6.65 ppm: d: 1 H; 7.40 ppm: s: 1 H; 7.45-7.70 ppm: m: 4 H; 8.05 ppm: s: 2 H; 9.05 ppm: s: 1 H; 10.00 ppm: s: 1 H; 10.55 ppm: s: 1 H; 10.75 ppm: bs: 2 H. |

TABLE 4

(I) [Structure: benzothiadiazole-NH-pyrimidine-pyridine with Ar2 and NH-C(O)-NH-R1]

| Compound | R1 | Ar2 | NMR characterization |
|---|---|---|---|
| 12 | tert-butyl | 2-bromo-6-chlorophenyl | 1.50 ppm: s: 9 H; 7.45 ppm: t: 1 H; 7.65 ppm: d: 1 H; 7.80 ppm: d: 1 H; 8.00 ppm: dd: 2 H; 8.15 ppm: s: 1 H; 8.25 ppm: s: 1 H; 9.20 ppm: s: 1 H; 9.30 ppm: s: 1 H; 10.75 ppm: s: 1 H; 10.85 ppm: s: 1 H. |
| 13 | ethyl | 2,6-dichlorophenyl | (DMSO + TFA deuterated) 1.15 ppm: t: 3 H; 3.35 ppm: qd: 2 H; 7.50-7.70 ppm: m: 3 H; 8.00 ppm: dd: 2 H; 8.45 ppm: s: 1 H; 9.00 ppm: s: 1 H; 9.30 ppm: s: 1 H. |
| 14 | tert-butyl | 2,6-dibromophenyl | 1.50 ppm: s: 9 H; 7.35 ppm: t: 1 H; 7.80 ppm: d: 2 H; 8.00 ppm: dd: 2 H; 8.15 ppm: s: 2 H; 9.15 ppm: s: 1 H; 9.30 ppm: s: 1 H; 10.75 ppm: s: 1 H; 10.85 ppm: s: 1 H. |
| 15 | ethyl | 2,6-dibromophenyl | 1.30 ppm: t: 3 H; 3.30 ppm: qd: 2 H; 7.35 ppm: t: 1 H; 7.80 ppm: d: 2 H; 8.00 ppm: dd: 2 H; 8.15 ppm: s: 1 H; 8.50 ppm: s: 1 H; 9.15 ppm: s: 1 H; 9.20 ppm: s: 1 H; 10.20 ppm: s: 1 H; 10.70 ppm: s: 1 H. |
| 16 | phenyl | 2,6-dichlorophenyl | 7.15 ppm: t: 1 H; 7.50-7.70 ppm: mt: 5 H; 7.75-8.10 ppm: mt: 4 H; 8.30 ppm: s: 1 H; 9.25 ppm: s: 1 H; 9.35 ppm: s: 1 H; 9.50 ppm: s: 1 H; 10.85 ppm: s: 1 H; 13.30 ppm: s: 1 H. |
| 17 | tert-butyl | 3,5-dimethoxyphenyl | 1.50 ppm: s: 9 H; 3.70 ppm: s: 6 H; 6.65 ppm: s: 3 H; 7.30 ppm: s: 1 H; 8.00 ppm: dd: 2 H; 8.20 ppm: s: 1 H; 9.20 ppm: s: 1 H; 9.30 ppm: s: 1 H; 10.50 ppm: s: 1 H; 10.70 ppm: s: 1 H. |
| 18 | tert-butyl | phenyl | 1.50 ppm: s: 9 H; 7.25 ppm: s: 1 H; 7.45-7.65 ppm: m: 5 H; 8.00 ppm: dd: 2 H; 8.20 ppm: s: 1 H; 9.20 ppm: s: 1 H; 9.35 ppm: s: 1 H; 10.50 ppm: s: 1 H; 10.75 ppm: s: 1 H. |
| 19 | tert-butyl | 2,6-dimethylphenyl | 1.45 ppm: s: 9 H; 2.00 ppm: s: 6 H; 6.55 ppm: s: 1 H; 7.20-7.40: m: 3 H; 7.95 ppm: dd: 2 H; 8.10 ppm: s: 1 H; 9.15 ppm: s: 1 H; 9.30 ppm: s: 1 H; 10.45 ppm: s: 1 H; 10.65 ppm: s: 1 H. |
| 20 | tert-butyl | 2,6-difluorophenyl | 1.45 ppm: s: 9 H; 7.15-7.30: mt: 2 H; 7.50-7.70 ppm: mt: 1 H; 7.95 ppm: dd: 2 H; 8.25 ppm: s: 1 H; 8.45 ppm: s: 1 H; 9.15 ppm: s: 1 H; 9.30 ppm: s: 1 H; 10.50 ppm: s: 1 H; 10.70 ppm: s: 1 H. |
| 21 | isopropyl | 2,6-dichlorophenyl | 1.35 ppm: d: 6 H; 3.80-4.00 ppm: mt: 1 H; 7.40-7.55 ppm: mt: 1 H; 7.60-7.65 ppm: mt: 2 H; 7.95 ppm: dd: 2 H; 8.15 ppm: s: 1 H; 8.60 ppm: s: 1 H; 9.15 ppm: s: 1 H; 9.25 ppm: s: 1 H; 10.45 ppm: d: 1 H; 10.75 ppm: s: 1 H. |

The compounds according to the invention were subjected to pharmacological assays for determining their anticancer activity.

The compounds of formula (I) according to the present invention were tested in vitro on a panel of tumour lines of human origin, originating:

from breast cancer: MDA-MB231 (American Type culture collection, Rockville, Md., USA, ATCC-HTB26), MDA-A1 or MDA-ADR (called multi-drug resistant MDR line, and described by E. Collomb et al., in Cytometry, 12(1):15-25, 1991), and MCF7 (ATCC-HTB22), from prostate cancer: DU145 (ATCC-HTB81) and PC3 (ATCC-CRL1435), from colon cancer: HCT116 (ATCC-CCL247) and HCT15 (ATCC-CCL225), from lung cancer: H460 (described by Carmichael in Cancer Research 47 (4):936-942, 1987 and provided by the National Cancer Institute, Frederick Cancer Research and Development Center, Frederick, Md., USA), from glioblastoma: SF268 (described by Westphal in Biochemical & Biophysical Research Communications 132 (1): 284-289, 1985 and provided by the National Cancer Institute, Frederick Cancer Research and Development Center, Frederick, Md., USA), from leukaemia: CMLT1 (described by Kuriyama et al. in Blood, 74: 1989, 1381-1387, by Soda et al. in British Journal of Haematology, 59: 1985, 671-679 and by Drexler, in Leukemia Research, 18: 1994, 919-927 and provided by the company DSMZ (Deutsche Sammlung von Mikroorganismen und Zellkulturen GmbH) Mascheroder Weg 1b, 38124 Braunschweig, Germany), K-562 (described by Lozzio et al., J Natl Cancer Inst 50: 535 (1973), by Lozzio et al., Blood 45: 321 (1975), and provided by DSMZ No. ACC 10), KG-1a (described by Koeffler et al., Blood 56: 265 (1980), and provided by DSMZ No. ACC 421), and Kasumi-1 (described by Asou et al., Blood 77: 2031 (1991), and provided by DSMZ No. ACC 220).

The cell proliferation and viability were determined in a test using 3-(4,5-dimethylthiazol-2-yl)-5-(3-carboxymethoxyphenyl)-2-(4-sulphophenyl)-2H-tetrazolium (MTS) according to Fujishita T. et al., Oncology, 2003, 64 (4), 399-406. In this test, the mitochondrial ability of the live cells to convert MTS to a coloured compound is measured after 72 hours of incubation of a compound of formula (I) according to the invention. The concentrations of compound according to the invention which result in a 50% loss of cell proliferation and cell viability ($IC_{50}$) are between 1 nM and 10 µM, depending on the tumor line and the compound tested. For example, compound No. 1 has an $IC_{50}$ of 40 nM on the K-562 line, an $IC_{50}$ of 50 nM on the KG-1a line and an $IC_{50}$ of 40 nM on the Kasumi-1 line. On the K-562 line, compound No. 5 has an $IC_{50}$ of 5 nM, compound No. 9 has an $IC_{50}$ of 19 nM, and compound No. 13 has an $IC_{50}$ of 74 nM. On the SF268, compound No. 7 has an $IC_{50}$ of 43 nM.

Thus, according to the present invention, it appears that the compounds of formula (I) bring about a loss of proliferation and of viability of the tumour cells. It therefore appears that the compounds according to the invention have an anticancer activity and an activity in the treatment of other proliferative diseases such as psoriasis, restenosis, atherosclerosis or AIDS, for example, and also in diseases caused by vascular smooth muscle cell proliferation and in rheumatoid arthritis.

Thus, according to another of its aspects, a subject of the invention is medicaments which comprise a compound of formula (I), or an addition salt of the latter with a pharmaceutically acceptable acid or a hydrate or a solvate of the compound of formula (I).

These medicaments find their use in therapeutics, in particular in the treatment or prevention of diseases caused or exacerbated by cell proliferation, and in particular tumour cell proliferation. A product in accordance with the invention may be used for the manufacture of a medicament that is of use in the treatment of a pathological state, in particular a cancer.

As an inhibitor of tumour cell proliferation, these compounds are of use in the prevention and treatment of leukaemias, both primary and metastatic solid tumours, carcinomas and cancers, in particular: breast cancer; lung cancer; cancer of the small intestine, colon cancer and rectal cancer; cancer of the respiratory tracts, of the oropharynx and of the hypopharynx; (esophageal cancer; liver cancer, stomach cancer, cancer of the bile ducts, gall bladder cancer, pancreatic cancer; cancer of the urinary tracts, including kidney, urothelium and bladder; cancers of the female genital tract, including uterine cancer, cervical cancer, ovarian cancer, chloriocarcinoma and trophoblastoma; cancers of the male genital tract, including prostate cancer, cancer of the seminal vesicles, testicular cancer, germinal cell tumours; cancers of the endocrine glands, including cancer of the thyroid, of the pituitary gland, of the adrenal glands; skin cancers, include hemangiomas, melanomas, sarcomas, including Kaposi's sarcoma; brain tumours, nerve tumours, eye tumours, meningeal tumours, including astrocytomas, gliomas, glioblastomas, retinoblastomas, neurinomas, neuroblastomas, schwannomas, meningiomas; malignant hematopoietic tumours; leukaemias, (acute lymphocytic leukaemia (ALL), acute myeloid leukaemia (AML), chronic myeloid leukaemia (CML), chronic lymphocytic leukaemia (CLL)), chloromas, plasmocytomas, T- or B-cell leukaemias, non-Hodgkin's lymphomas or Hodgkin's lymphomas, myelomas, various malignant hemopathies.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient. A pharmaceutical composition can also contain, in addition, another anticancer ingredient.

Said excipients are selected according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its optional salt, solvate or hydrate, can be administered in unit administration form, as a mixture with conventional pharmaceutical excipients, to animals and to human beings for the prophylaxis or the treatment of the conditions or diseases above.

Appropriate unit administration forms include the oral administration forms such as tablets, soft or hard gelatin capsules, powders, granules and oral solutions or suspensions, sublingual, buccal, intratracheal, intraocular and intranasal administration forms, forms of administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in the form of a tablet can comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The compounds of formula (I) above can be used at daily doses of 0.002 to 2000 mg per kilogram of body weight of the mammal to be treated, preferably at daily doses of 0.1 to 300 mg/kg. In human beings, the dose can range preferably from 0.02 to 10 000 mg per day, more particularly from 1 to 3000 mg, depending on the age of the individual to be treated or the type of treatment: prophylactic or curative.

There may be specific cases where higher or lower dosages are appropriate: such dosages do not depart from the scope of the invention. According to the usual practice, the dosage appropriate to each patient is determined by the physician according to the method of administration, and the weight and response of said patient.

According to another of its aspects, the present invention also relates to a method of treatment of the pathologies indicated above, which comprises the administration, to a patient, of an effective dose of a compound according to the invention, or one of its pharmaceutically acceptable salts or hydrates or solvates.

According to the present invention, the compound(s) of formula (I) can be administered in combination with one (or more) anticancer active ingredient(s), in particular antitumour compounds such as alkylating agents, for instance alkylsulphonates (busulphan), dacarbazine, procarbazine, nitrogenous mustards (chlormethine, melphalan, chlorambucil), cyclophosphamide, ifosfamide; nitrosoureas such as carmustine, lomustine, semustine, streptozocin; antineoplastic alkaloids such as vincristine, vinblastine; taxanes such as paclitaxel or taxotere; antineoplastic antibiotics such as actinomycin; intercalating agents, antineoplastic antimetabolites, folate antagonists, methotrexate; purine synthesis inhibitors; purine analogues such as mercaptopurine, 6-thioguanine; pyrimidine synthesis inhibitors, aromatase inhibitors, capecitabine, pyrimidine analogues such as fluorouracil, gemcitabine, cytarabine and cytosine arabinoside; brequinar; topoisomerase inhibitors such as camptothecin or etoposide; anticancer hormone agonists and antagonists including tamoxifen; kinase inhibitors, imatinib; growth factor inhibitors; anti-inflammatories such as pentosane polysulphate, corticosteroids, prednisone, dexamethasone; antitopoisomerases such as etoposide, anthracyclines including doxorubicin, bleomycin, mitomycin and methramycin; anticancer metal complexes, platinum complexes, cisplatin, carboplatin, oxaliplatin; interferon alpha, triphenylthiophosphoramide, altretamine; antiangiogenic agents; thalidomide; immunotherapy adjuvants; vaccines.

According to the present invention, the compounds of formula (I) can also be administered in combination with one or more other active ingredients that are of use in one of the pathologies indicated above, for example an anti-emetic agent, pain-killer, anti-inflammatory, or anti-cachexia agent.

It is also possible to combine with the compounds of the present invention a radiation treatment. These treatments can be administered simultaneously, separately or sequentially. The treatment will be adapted by the practitioner according to the disease to be treated.

What is claimed is:
1. A compound according to formula (I):

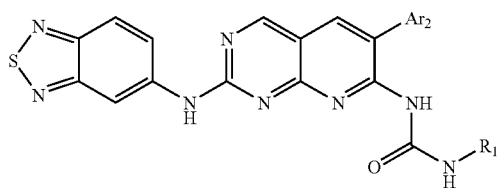

(I)

wherein:
R1 is tert-butyl and Ar2 is 2,6-dichlorophenyl; or
R1 is tert-butyl and Ar2 is 2-bromo-6-chlorophenyl; or
R1 is ethyl and Ar2 is 2,6-dichlorophenyl; or
R1 is tert-butyl and Ar2 is 2,6-dibromophenyl; or
R1 is ethyl and Ar2 is 2,6-dibromophenyl; or
R1 is phenyl and Ar2 is 2,6-dichlorophenyl; or
R1 is tert-butyl and Ar2 is 3,5-dimethoxyphenyl; or
R1 is tert-butyl and Ar2 is phenyl; or
R1 is tert-butyl and Ar2 is 2,6-dimethylphenyl; or
R1 is tert-butyl and Ar2 is 2,6-difluorophenyl; or
R1 is isopropyl and Ar2 is 2,6-dichlorophenyl;
or a pharmaceutically acceptable salt thereof.

2. A compound according to claim 1, which is:

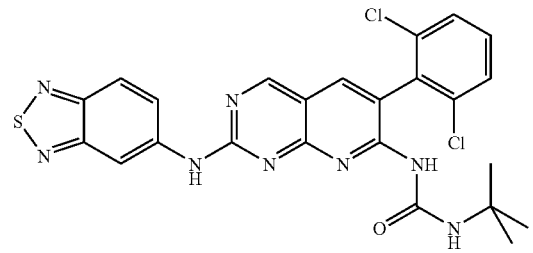

or a pharmaceutically acceptable salt thereof.

3. A compound selected from the group consisting of:
N-[2-(2,1,3-benzothiadiazol-5-ylamino)-6-(2-bromo-6-chlorophenyl)pyrido[2,3-d]pyrimidin-7-yl]-N'-(1,1-dimethylethyl)urea;
N-[2-(2,1,3-benzothiadiazol-5-ylamino)-6-(2,6-dichlorophenyl)pyrido[2,3-d]pyrimidin-7-yl]-N'-ethylurea;
N-[2-(2,1,3-benzothiadiazol-5-ylamino)-6-(2,6-dibromophenyl)pyrido[2,3-d]pyrimidin-7-yl]-N'-(1,1-dimethylethyl)urea;
N-[2-(2,1,3-benzothiadiazol-5-ylamino)-6-(2,6-dibromophenyl)pyrido[2,3-d]pyrimidin-7-yl]-N'-ethylurea;
N-[2-(2,1,3-benzothiadiazol-5-ylamino)-6-(2,6-dichlorophenyl)pyrido[2,3-d]pyrimidin-7-yl]-N'-phenylurea;
N-[2-(2,1,3-benzothiadiazol-5-ylamino)-6-(3,5-dimethoxyphenyl)pyrido[2,3-d]pyrimidin-7-yl]-N'-(1,1-dimethylethyl)urea;
N-[2-(2,1,3-benzothiadiazol-5-ylamino)-6-phenylpyrido[2,3-d]pyrimidin-7-yl]-N'-(1,1-dimethylethyl)urea;
N-[2-(2,1,3-benzothiadiazol-5-ylamino)-6-(2,6-dimethylphenyl)pyrido[2,3-d]pyrimidin-7-yl]-N'-(1,1-dimethylethyl)urea;
N-[2-(2,1,3-benzothiadiazol-5-ylamino)-6-(2,6-difluorophenyl)pyrido[2,3-d]pyrimidin-7-yl]-N'-(1,1-dimethylethyl)urea; and
N-[2-(2,1,3-benzothiadiazol-5-ylamino)-6-(2,6-dichlorophenyl)pyrido[2,3-d]pyrimidin-7-yl]-N'-(1-methylethyl)urea;
or a pharmaceutically acceptable salt thereof.

4. A pharmaceutical composition comprising a compound according to claim 1 or a pharmaceutically acceptable salt thereof; and at least one pharmaceutically acceptable excipient.

5. A pharmaceutical composition comprising a compound according to claim 3 or a pharmaceutically acceptable salt thereof; and at least one pharmaceutically acceptable excipient.

6. A pharmaceutical composition comprising a compound according to claim 2 or a pharmaceutically acceptable salt thereof; and at least one pharmaceutically acceptable excipient.

* * * * *

UNITED STATES PATENT AND TRADEMARK OFFICE
CERTIFICATE OF CORRECTION

PATENT NO. : 7,504,406 B2
APPLICATION NO. : 11/955583
DATED : March 17, 2009
INVENTOR(S) : Bernard Bourrie et al.

It is certified that error appears in the above-identified patent and that said Letters Patent is hereby corrected as shown below:

In column 3, line 23, delete "Br." and insert -- Br, --, therefor.

In column 3, line 60, after "urea)" insert -- . --.

In column 5, line 64, delete "LiAlH$_4$" and insert -- LiAlH$_4$ --, therefor.

In column 6, line 31, delete "Ar'$_1$NH2" and insert -- Ar'$_1$NH$_2$ --, therefor.

In column 7, line 34, delete "MH+:" and insert -- MH$^+$: --, therefor.

In column 12, line 18, delete "15" and insert -- 15 minutes --, therefor.

In column 17, line 30, delete "Compound No. 6" and insert -- (Compound No. 6) --, therefor.

In column 17, line 55, delete "eluant" and insert -- eluent --, therefor.

In column 18, line 28, delete "MH+" and insert -- MH$^+$ --, therefor.

In column 18, line 43, delete "Compounds No. 12-21" and insert -- (Compounds No. 12-21) --, therefor.

In column 25, line 38, delete "(esophageal" and insert -- esophageal --, therefor.

In column 25, line 42-43, delete "chloriocarcinoma" and insert -- choriocarcinoma --, therefor.

In column 25, line 56-57, delete "antitumour" and insert -- antitumor --, therefor.

In column 27, line 9, delete "methramycin;" and insert -- mithramycin --, therefor.

Signed and Sealed this
Third Day of April, 2012

David J. Kappos
*Director of the United States Patent and Trademark Office*